United States Patent
Chin (10) Patent No.: US 11,547,607 B2
(45) Date of Patent: Jan. 10, 2023

(54) GOGGLE AND ANGLE ADJUSTMENT MECHANISM THEREOF

(71) Applicant: ASWAN INTERNATIONAL CORP., Taipei (TW)

(72) Inventor: Meng-Hsien Chin, Taipei (TW)

(73) Assignee: ASWAN INTERNATIONAL CORP., Taipei (TW)

( * ) Notice: Subject to any disclaimer, the term of this patent is extended or adjusted under 35 U.S.C. 154(b) by 18 days.

(21) Appl. No.: 17/209,340

(22) Filed: Mar. 23, 2021

(65) Prior Publication Data
US 2022/0304860 A1    Sep. 29, 2022

(51) Int. Cl.
*A61F 9/02* (2006.01)

(52) U.S. Cl.
CPC .............. *A61F 9/027* (2013.01); *A61F 9/029* (2013.01)

(58) Field of Classification Search
CPC . A61F 9/02; A61F 9/027; A61F 9/029; G02C 5/146; G02C 5/16; G02C 5/20
See application file for complete search history.

(56) References Cited

U.S. PATENT DOCUMENTS

| | | | | |
|---|---|---|---|---|
| 2,668,291 A * | 2/1954 | Schauweker | ........... | A61F 9/027 351/121 |
| 3,212,102 A * | 10/1965 | Muller | .................... | A61F 9/045 351/120 |
| 5,357,292 A * | 10/1994 | Wiedner | ................. | G02C 1/02 351/115 |
| 5,381,192 A * | 1/1995 | Canavan | .................. | G02C 5/20 351/111 |
| 5,483,303 A * | 1/1996 | Hirschman | .............. | G02C 1/04 351/85 |
| 5,528,320 A * | 6/1996 | Specht | ................. | G02C 5/2272 351/92 |
| 5,530,490 A * | 6/1996 | Canavan | ................... | A61F 9/02 351/120 |
| 5,555,037 A * | 9/1996 | Canavan | .................. | G02C 5/20 351/111 |
| 5,565,937 A * | 10/1996 | Lee | ....................... | G02C 5/2263 351/120 |
| 5,638,147 A * | 6/1997 | Wang-Lee | ............... | G02C 5/10 351/120 |

(Continued)

FOREIGN PATENT DOCUMENTS

DE    20207349 U1    8/2002

*Primary Examiner* — F Griffin Hall
(74) *Attorney, Agent, or Firm* — Li & Cai Intellectual Property (USA) Office (57) ABSTRACT

A goggle and an angle adjustment mechanism thereof are provided. The angle adjustment mechanism includes an assembling slot and a bendable temple. The assembling slot has a retaining rack arranged therein, and the retaining rack is in an arced shape. The bendable temple is integrally formed as a single one-piece structure and includes an assembling segment pivotally connected to the assembling slot and having an engaging tooth and a flexible segment that extends from the assembling segment. The engaging tooth of the assembling segment is inserted into the assembling slot and is engaged with the retaining rack, and the assembling segment is rotatable relative to the assembling slot in an angle range, so that the engaging tooth is engaged with and movable from one end of the retaining rack to another end of the retaining rack.

16 Claims, 13 Drawing Sheets

(56) References Cited

U.S. PATENT DOCUMENTS

| | | | | |
|---|---|---|---|---|
| 5,661,535 A * | 8/1997 | Wang | G02C 5/146 | 351/110 |
| 5,760,867 A * | 6/1998 | Pernicka | G02C 5/2263 | 351/149 |
| 5,796,461 A * | 8/1998 | Stepan | G02C 5/20 | 351/86 |
| 5,812,234 A * | 9/1998 | Carswell | G02C 5/20 | 351/120 |
| 5,870,165 A * | 2/1999 | Wang | G02C 1/02 | 351/110 |
| 5,946,072 A * | 8/1999 | Canavan | G02C 5/2263 | 351/110 |
| 6,086,200 A * | 7/2000 | Wang-Lee | G02C 5/2263 | 351/111 |
| 6,290,356 B1 * | 9/2001 | Chi | G02C 5/2263 | 351/110 |
| 6,454,406 B1 * | 9/2002 | Guo | G02C 5/2263 | 351/120 |
| 6,467,902 B2 * | 10/2002 | Wang-Lee | G02C 5/2263 | 351/110 |
| 6,474,813 B1 * | 11/2002 | Yeh | G02C 5/2263 | 351/111 |
| 6,543,896 B1 * | 4/2003 | Huang | G02C 5/20 | 351/111 |
| 6,776,483 B1 * | 8/2004 | Wu | G02C 5/2263 | 351/120 |
| 6,863,396 B1 * | 3/2005 | Chen | G02C 5/2209 | 351/110 |
| 6,883,914 B1 * | 4/2005 | Yang | G02C 5/2263 | 351/120 |
| 6,994,434 B2 * | 2/2006 | Blanchette | G02C 5/10 | 351/110 |
| 7,104,646 B2 * | 9/2006 | Yang | G02C 5/20 | 351/120 |
| 7,144,109 B2 * | 12/2006 | Bruck | G02C 5/2263 | 351/120 |
| 7,300,150 B1 * | 11/2007 | Chen | G02C 5/2263 | 351/120 |
| 7,625,082 B2 * | 12/2009 | Kawanishi | G02C 5/143 | 351/120 |
| 7,896,491 B1 * | 3/2011 | Lin | G02C 5/2263 | 351/120 |
| 8,070,287 B1 * | 12/2011 | Wang-Lee | G02C 5/146 | 351/63 |
| 2002/0085171 A1 * | 7/2002 | Wang-Lee | G02C 5/20 | 351/120 |
| 2004/0141149 A1 * | 7/2004 | Blanchette | G02C 9/04 | 351/99 |

* cited by examiner

GOGGLE AND ANGLE ADJUSTMENT MECHANISM THEREOF

FIELD OF THE DISCLOSURE

The present disclosure relates to a goggle, and more particularly to a goggle and an angle adjustment mechanism thereof for adjusting an angle of at least one temple thereof.

BACKGROUND OF THE DISCLOSURE

A conventional goggle needs to have an adjustment function for matching different facial sizes and contours of users. For example, the conventional goggle includes a frame and two temple structures that are assembled to the frame, and each of the two temple structures is formed by assembling a plurality of components, thereby providing an angle adjustment function. However, the temple structure of the conventional goggle is manufactured by a complex assembling process and is easily damaged, which results in a high manufacturing cost of the conventional goggle.

SUMMARY OF THE DISCLOSURE

In response to the above-referenced technical inadequacy, the present disclosure provides a goggle and an angle adjustment mechanism thereof to effectively improve on the issues associated with conventional goggles.

In one aspect, the present disclosure provides a goggle, which includes a lens, two lateral frames, a top frame, and two bendable temples. The two lateral frames are respectively connected to two opposite sides of the lens. Two sides of the two lateral frames away from each other each have an assembling slot. The assembling slot of each of the two lateral frames has a retaining rack arranged therein, and the retaining rack is in an arced shape and is arranged adjacent to the lens. The top frame is connected to the lens and the two lateral frames. The lens, the two lateral frames, and the top frame jointly define an eye-protection space. Each of the two bendable temples is integrally formed as a single one-piece structure and includes an assembling segment having an engaging tooth and a flexible segment that extends from the assembling segment. The assembling segments of the two bendable temples are respectively and pivotally connected to the assembling slots of the two lateral frames, and each of the two bendable temples and the corresponding assembling slot are jointly defined as an angle adjustment mechanism. In each of the two angle adjustment mechanisms, the engaging tooth of the assembling segment is inserted into the assembling slot and is engaged with the retaining rack, and the assembling segment is rotatable relative to the assembling slot in an angle range, so that the engaging tooth is engaged with and movable from one end of the retaining rack to another end of the retaining rack.

In another aspect, the present disclosure provides an angle adjustment mechanism of a goggle, which includes an assembling slot and a bendable temple. The assembling slot has a retaining rack arranged therein. The retaining rack is in an arced shape. The bendable temple is integrally formed as a single one-piece structure and includes an assembling segment pivotally connected to the assembling slot, and a flexible segment that extends from the assembling segment, wherein the assembling segment has an engaging tooth. The engaging tooth of the assembling segment is inserted into the assembling slot and is engaged with the retaining rack, and the assembling segment is rotatable relative to the assembling slot in an angle range, so that the engaging tooth is engaged with and movable from one end of the retaining rack to another end of the retaining rack.

Therefore, the goggle of the present disclosure is provided with the angle adjustment mechanism that is structurally simplified (e.g., the bendable temple formed as a single one-piece structure is pivotally connected to the assembling slot through the assembling segment, and the engaging tooth is movably engaged with the retaining rack), thereby effectively reducing manufacturing cost thereof and probability of being damaged.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way.

Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 1:
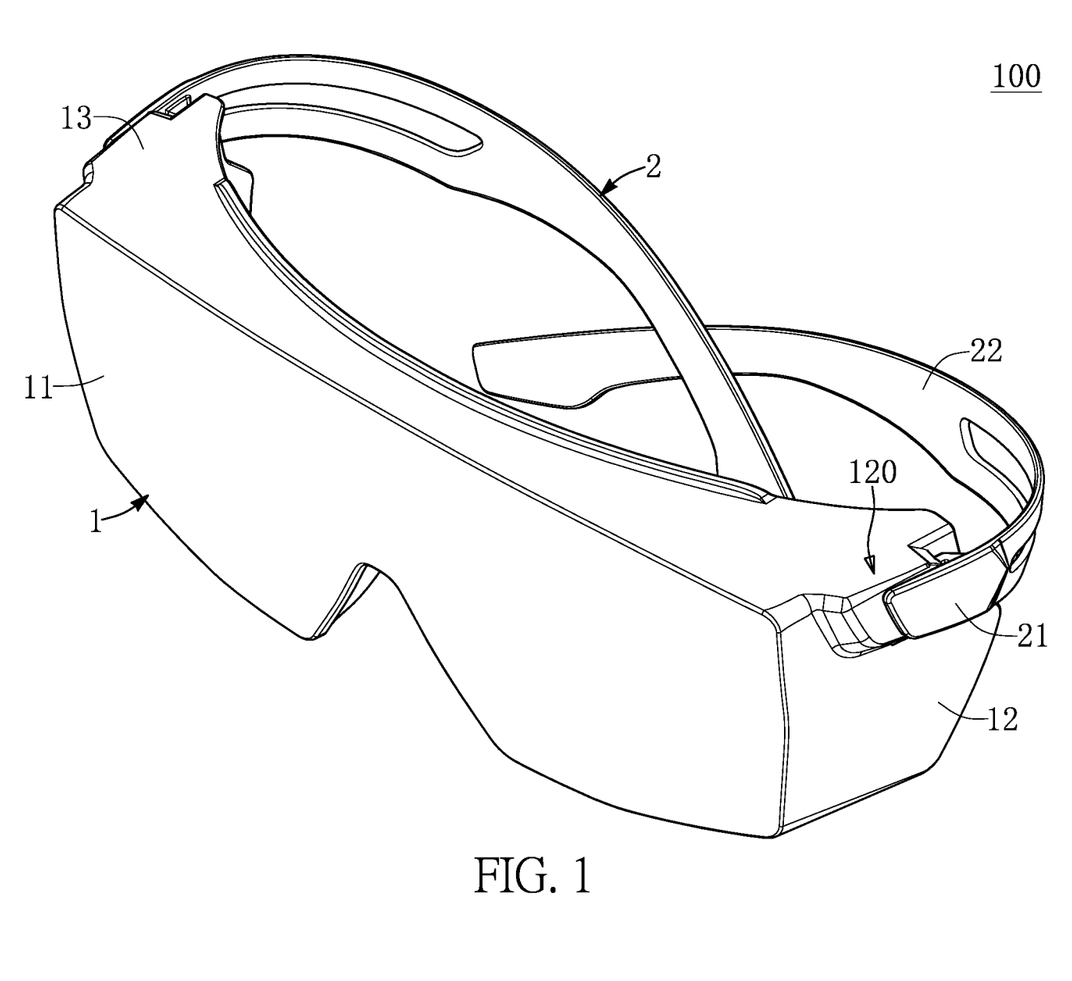
FIG. 1 is a perspective view of a goggle according to a first embodiment of the present disclosure.
Figure 2:
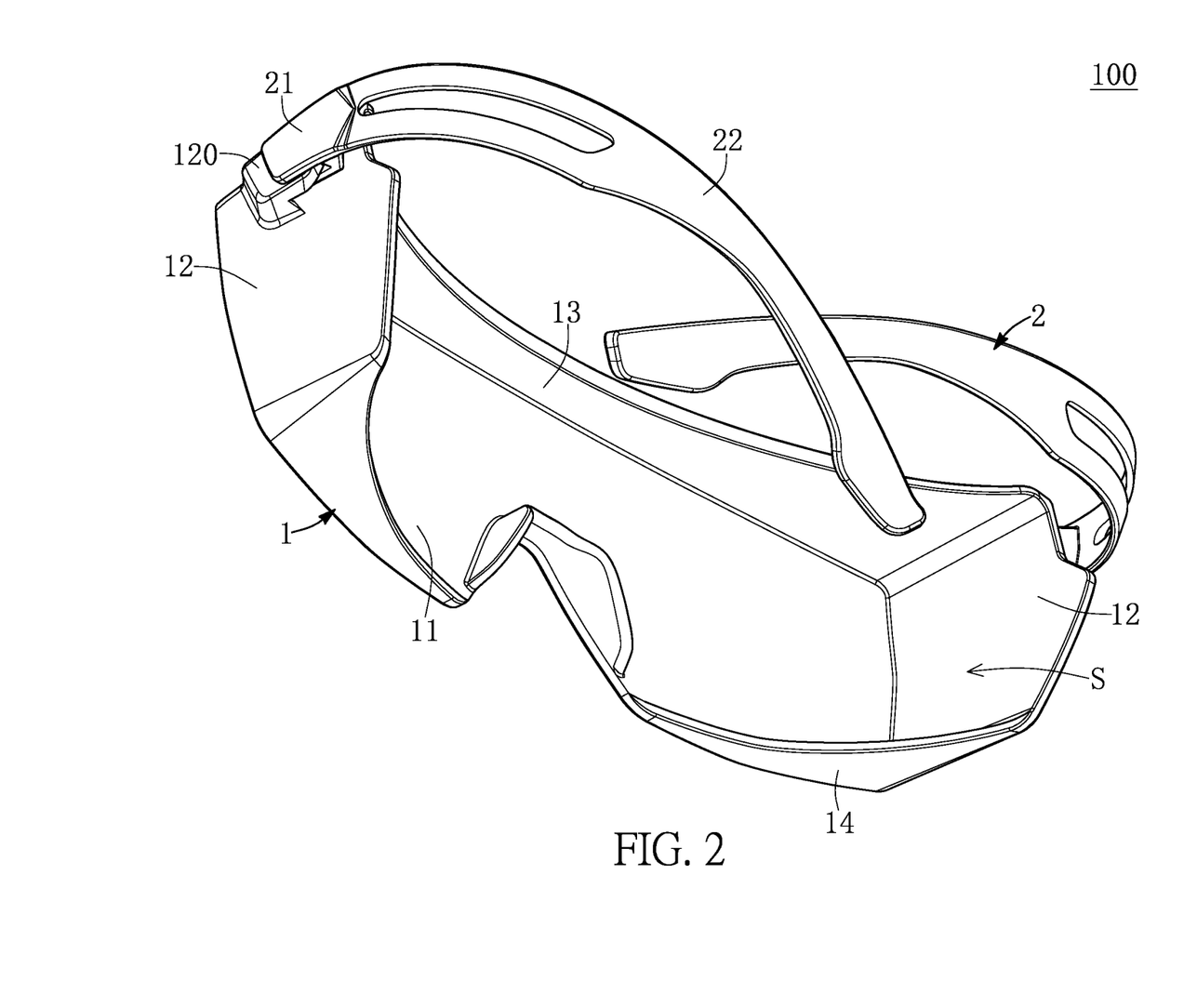
FIG. 2 is a perspective view showing the goggle of FIG. 1 from another angle of view.

Referring to FIG. 1 to FIG. 11, a first embodiment of the present disclosure provides a goggle 100. As shown in FIG. 1 and FIG. 2, the goggle 100 in the present embodiment is used for being worn on (e.g., attached to) a user's face to protect the user's face (e.g., the user's eyes). The goggle 100 in the present embodiment includes a lens assembly 1 and two bendable temples 2 that are detachably assembled to the lens assembly 1. The following description describes the structure and connection relationship of each of the lens assembly 1 and the two bendable temples 2.

Figure 3:
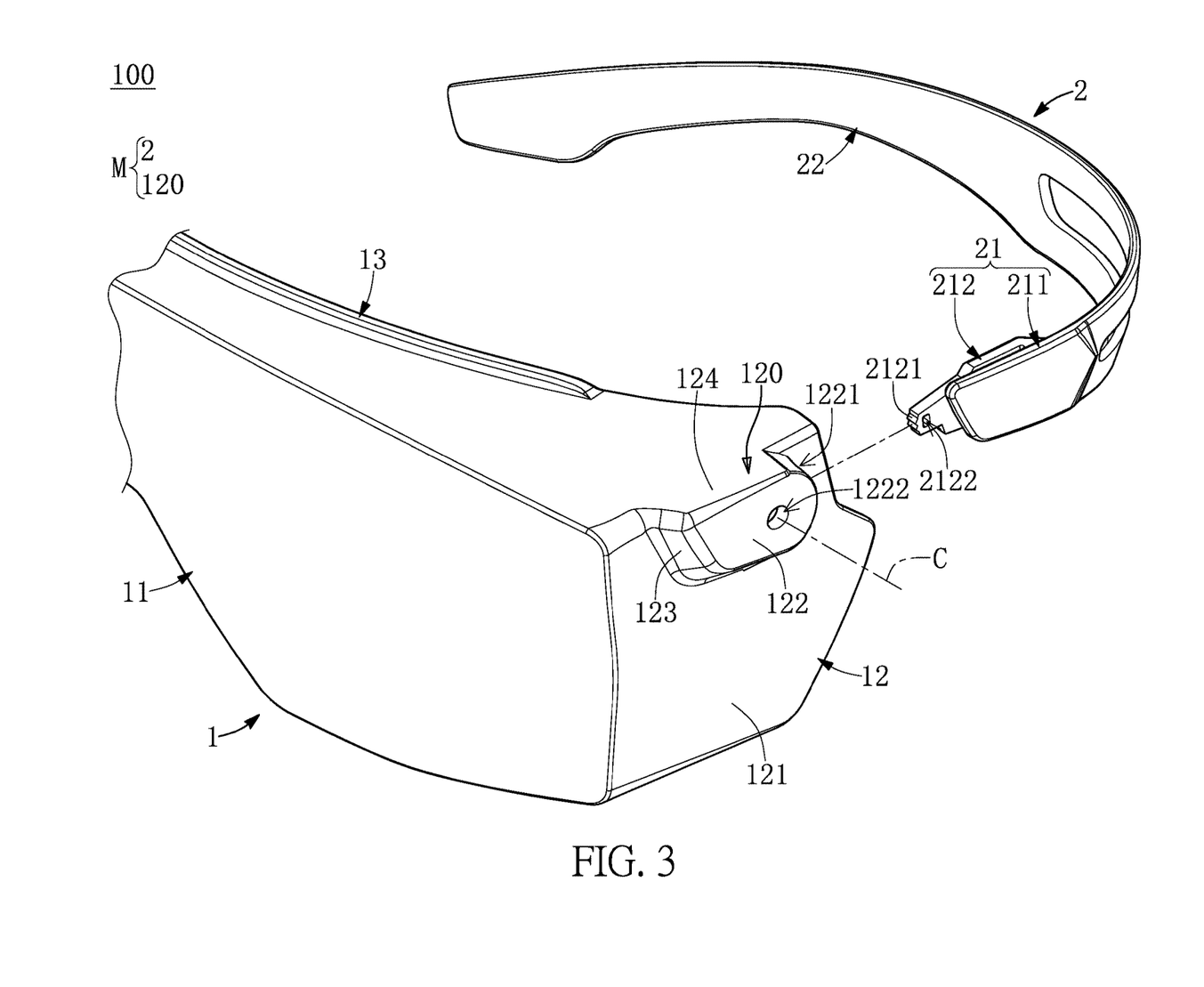
FIG. 3 is a partial exploded view of FIG. 1.

As shown in FIG. 1 to FIG. 3, the lens assembly 1 includes a lens 11, two lateral frames 12 respectively connected to two opposite sides of the lens 11, a top frame 13 connected to a top edge of the lens 11 and the two lateral frames 12, and a bottom frame 14 that is connected to a bottom edge of the lens 11 and the two lateral frames 12. The lens 11, the two lateral frames 12, the top frame 13, and the bottom frame 14 jointly define an eye-protection space S.

It should be noted that the lens assembly 1 (e.g., the lens 11, the two lateral frames 12, the top frame 13, and the bottom frame 14) in the present embodiment is light-permeable and is integrally formed as a single one-piece structure, but the present disclosure is not limited thereto. For example, in other embodiments of the present disclosure not shown in the drawings, the lens assembly 1 can be provided without the bottom frame 14; or, the lens assembly 1 can be provided by assembling a plurality of components (e.g., the lens 11 can be assembled in an annular frame that is formed by the two lateral frames 12, the top frame 13, and the bottom frame 14).

Two sides of the two lateral frames 12 away from each other each have an assembling slot 120. As the two lateral frames 12 in the present embodiment are of the substantially same structure and are mirror-symmetrical to each other, the following description discloses the structure of just one of the two lateral frames 12 for the sake of brevity, but the present disclosure is not limited thereto. For example, in other embodiments of the present disclosure not shown in the drawings, the two lateral frames 12 can be of different structures.

The lateral frame 12 in the present embodiment includes a main board 121, a limiting lateral board 122 facing the main board 121, and a limiting end portion 123 connecting the main board 121 and the limiting lateral board 122, and a limiting top board 124 that is coplanar with the top frame 13. The limiting top board 124 in the present embodiment is integrally connected to the main board 121, the limiting end portion 123, and the limiting lateral board 122.

Figure 4:
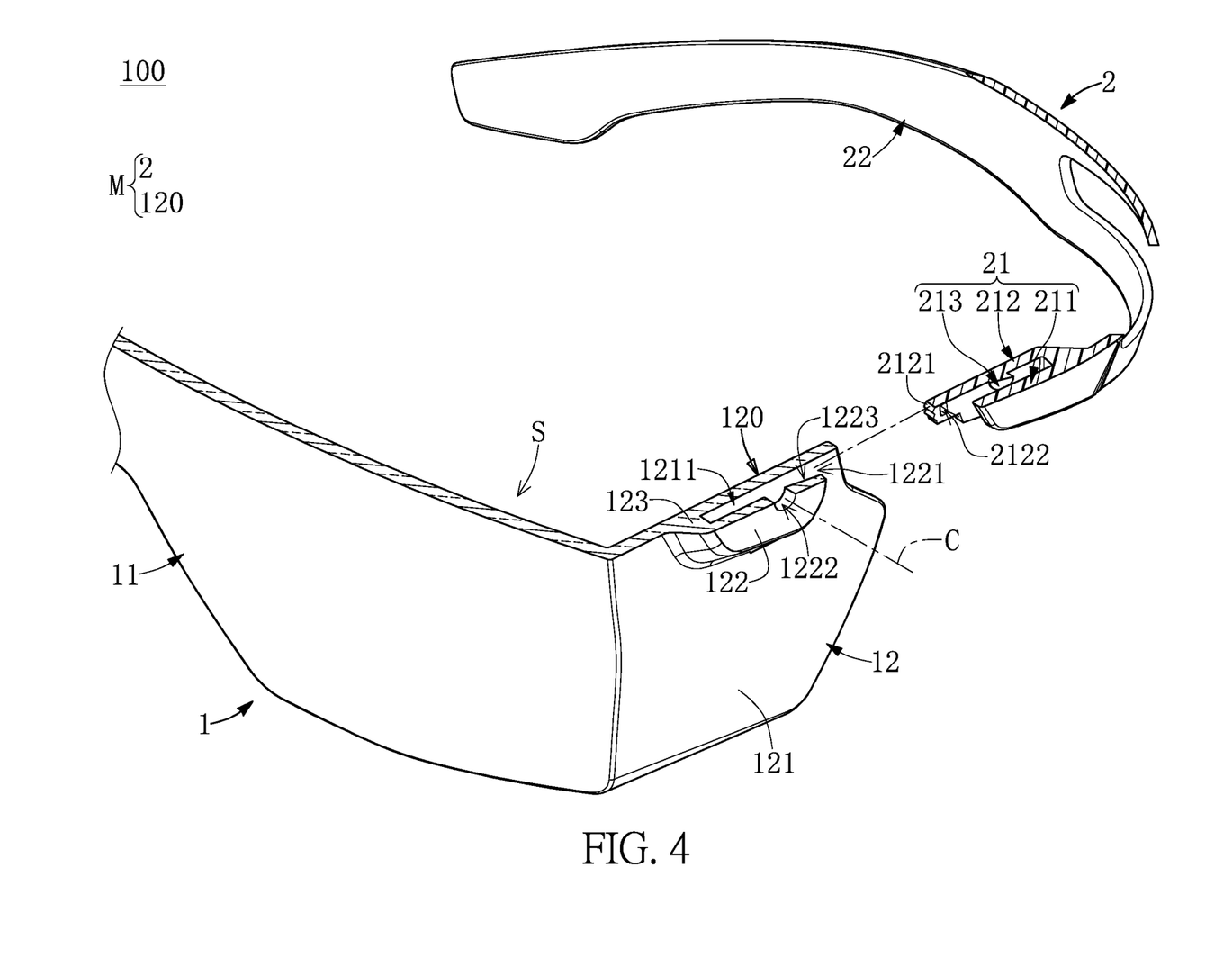
FIG. 4 is a perspective cross-sectional view of FIG. 3.
Figure 5:
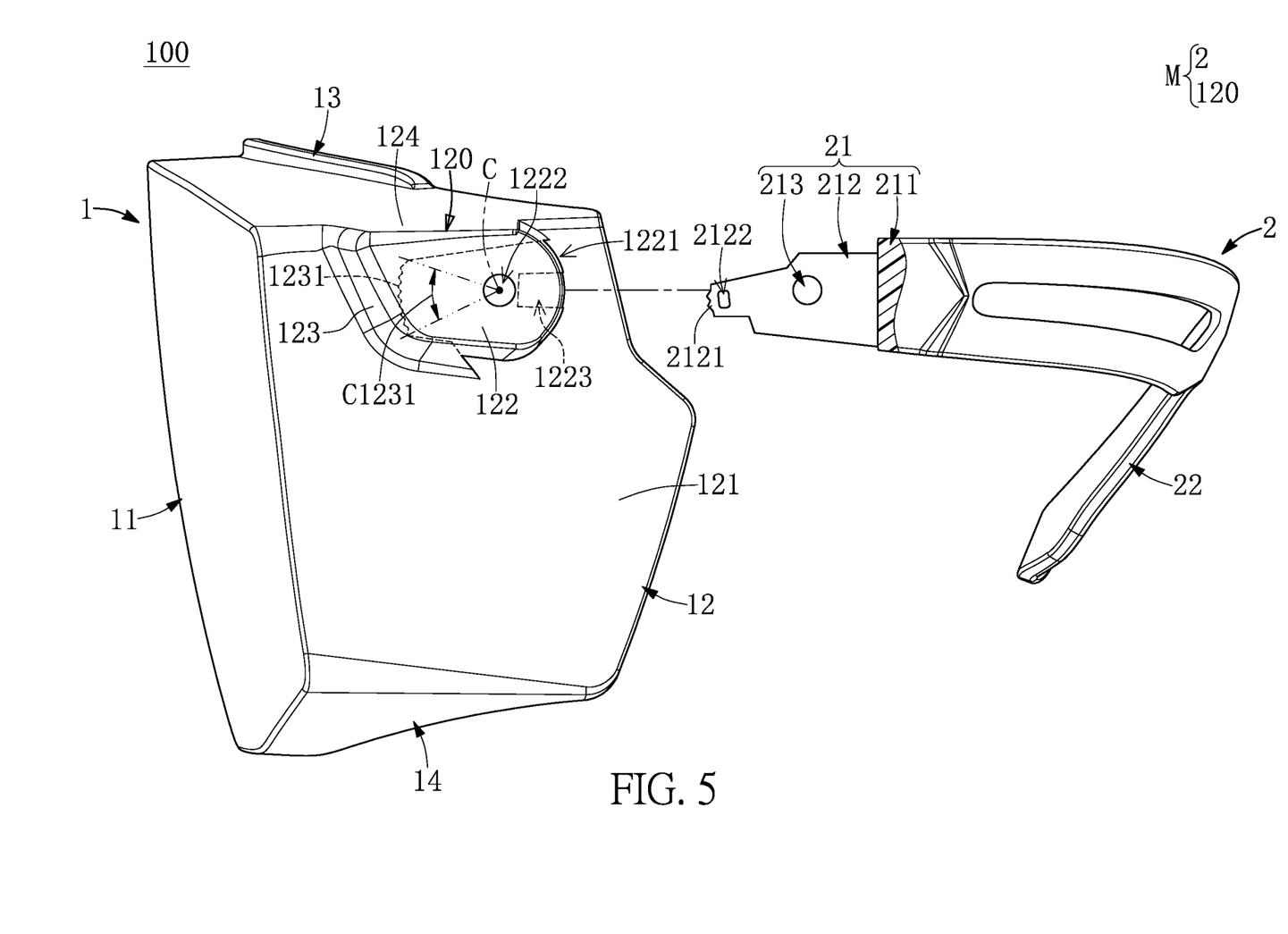
FIG. 5 is a planar view of FIG. 3.
Figure 6:
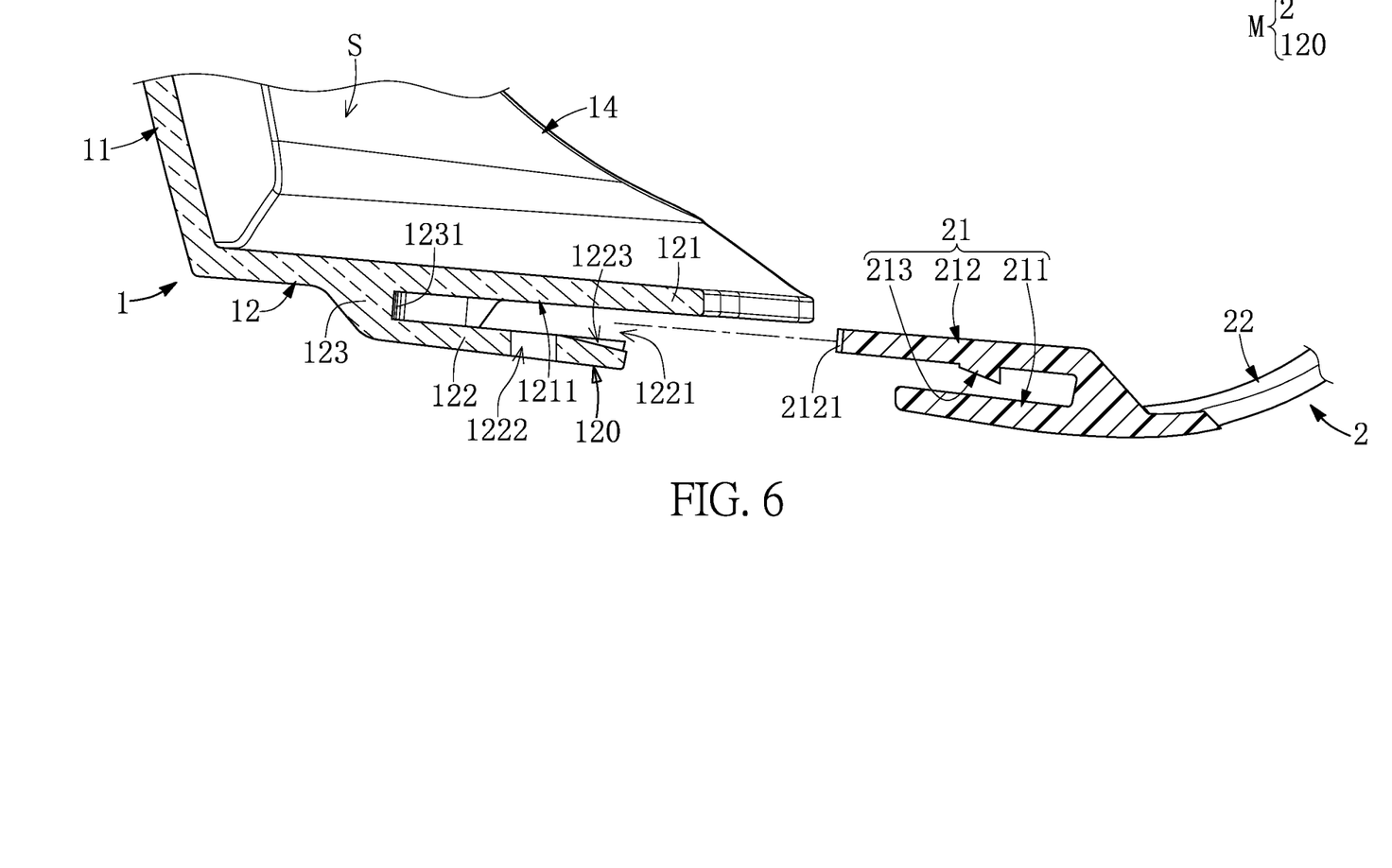
FIG. 6 is a planar view of FIG. 4.

As shown in FIG. 4 to FIG. 6, the assembling slot 120 includes the limiting lateral board 122, the limiting end portion 123, the limiting top board 124, and a mating portion 1211 of the main board 121 that faces the limiting lateral board 122. In other words, a bottom of the assembling slot 120 in the present embodiment is a hollow region, thereby preventing any attachment (e.g., a chemical agent) from existing in the assembling slot 120 after the assembling slot 120 is formed, but the present disclosure is not limited thereto. For example, in other embodiments of the present disclosure not shown in the drawings, the lateral frame 12 (or the assembling slot 120) can be provided without the limiting top board 124, so that a top and a bottom of the assembling slot 120 are hollow regions.

Specifically, the assembling slot 120 has a retaining rack 1231 arranged therein, and the retaining rack 1231 is in an arced shape and is arranged adjacent to the lens 11. The assembling slot 120 has a slot opening 1221 arranged on an end of the limiting lateral board 122 away from the limiting end portion 123. The retaining rack 1231 is formed on the limiting end portion 123 and faces the slot opening 1221.

Moreover, the limiting lateral board 122 has a shaft hole 1222. The limiting lateral board 122 has a guiding groove 1223 recessed from the end thereof toward the shaft hole 1222. The guiding groove 1223 is in spatial communication with the slot opening 1221, and a distance between the guiding groove 1223 and the mating portion 1211 gradually reduces in a direction from the slot opening 1221 to the shaft hole 1222. The shaft hole 1222 in the present embodiment is formed by penetrating the limiting lateral board 122 along an axis C, and the retaining rack 1231 has a center of circle located at the axis C, but the present disclosure is not limited thereto. For example, in other embodiments of the present disclosure not shown in the drawings, the shaft hole 1222 can be recessed in an inner surface of the limiting lateral board 122, but the shaft hole 1222 does not penetrate through the limiting lateral board 122.

The assembling slots 120 of the lens assembly 1 in the present embodiment are respectively assembled to the two bendable temples 2, but the present disclosure is not limited thereto. Each of the two bendable temples 2 and the corresponding assembling slot 120 are jointly defined as an angle adjustment mechanism M. In other embodiments of the present disclosure not shown in the drawings, the angle adjustment mechanism M can be applied to a structure other than the lens assembly 1 shown in the drawings of the present embodiment according to design requirements.

Figure 7:
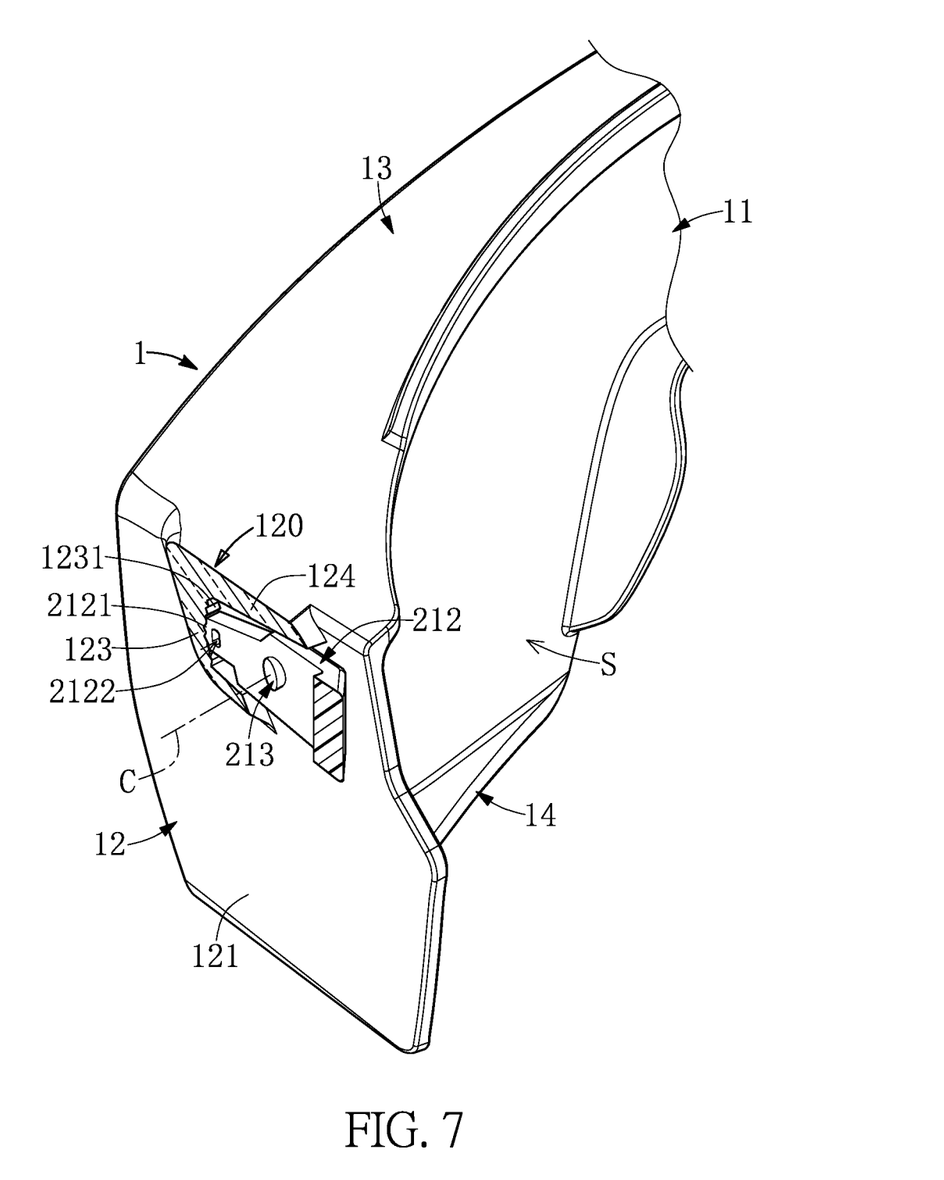
FIG. 7 is a perspective cross-sectional view showing a portion of the goggle according to the first embodiment of the present disclosure.
Figure 8:
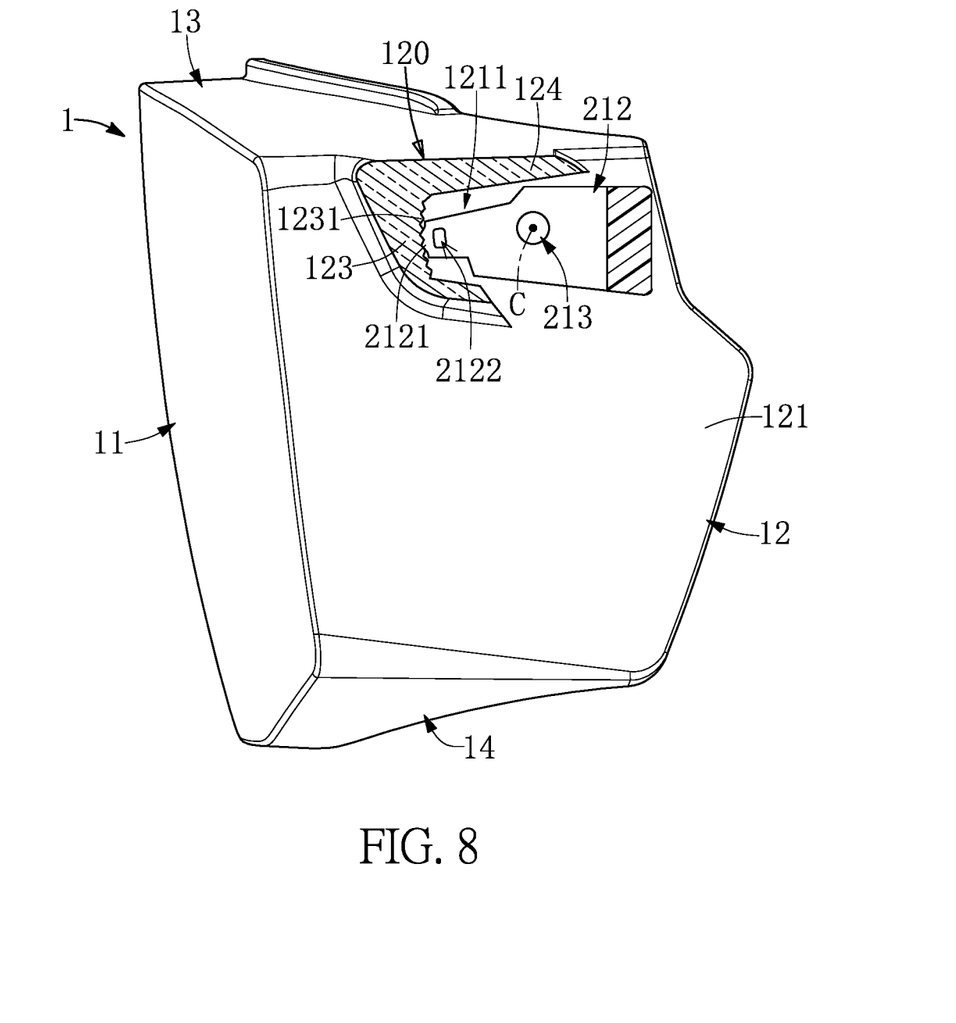
FIG. 8 is a planar view of FIG. 7.

Specifically, as shown in FIG. 6 to FIG. 8, each of the two bendable temples 2 is integrally formed as a single one-piece structure, and each of the two bendable temples 2 in the present embodiment is made of a single material, but the present disclosure is not limited thereto. Each of the two bendable temples 2 includes an assembling segment 21 and a flexible segment 22 that extends from the assembling segment 21. The two assembling segments 21 are respectively and pivotally connected to the assembling slots 120 of the two lateral frames 12. The flexible segment 22 of each of the two bendable temples 2 curvedly extends from the assembling segment 21 toward the lens 11 (as shown in FIG. 1), so that the flexible segments 22 of the two bendable temples 2 of the goggle 100 can contact with each other.

As the two bendable temples 2 in the present embodiment are of the substantially same structure and are mirror-symmetrical to each other with respect to the lens assembly 1, the following description discloses the structure of just one of the two bendable temples 2 (and the corresponding angle adjustment mechanism M) for the sake of brevity, but the present disclosure is not limited thereto. For example, in other embodiments of the present disclosure not shown in the drawings, the two bendable temples 2 can be of different structures.

As shown in FIG. 6 to FIG. 9, the assembling segment 21 in the present embodiment includes a shielding sheet 211 connected to the flexible segment 22, an L-shaped arm 212 connected to an inner side of the shielding sheet 211, and a rotation shaft 213 that is formed on an inner side of the L-shaped arm 212. In other words, the rotation shaft 213 is located between the L-shaped arm 212 and the shielding sheet 211. Moreover, a part of the L-shaped arm 212 is inserted into the assembling slot 120, the rotation shaft 213 of the assembling segment 21 is assembled to the shaft hole 1222, the L-shaped arm 212 and the shielding sheet 211 jointly sandwich the limiting lateral board 122, and the shielding sheet 211 covers the shaft hole 1222.

Figure 9:
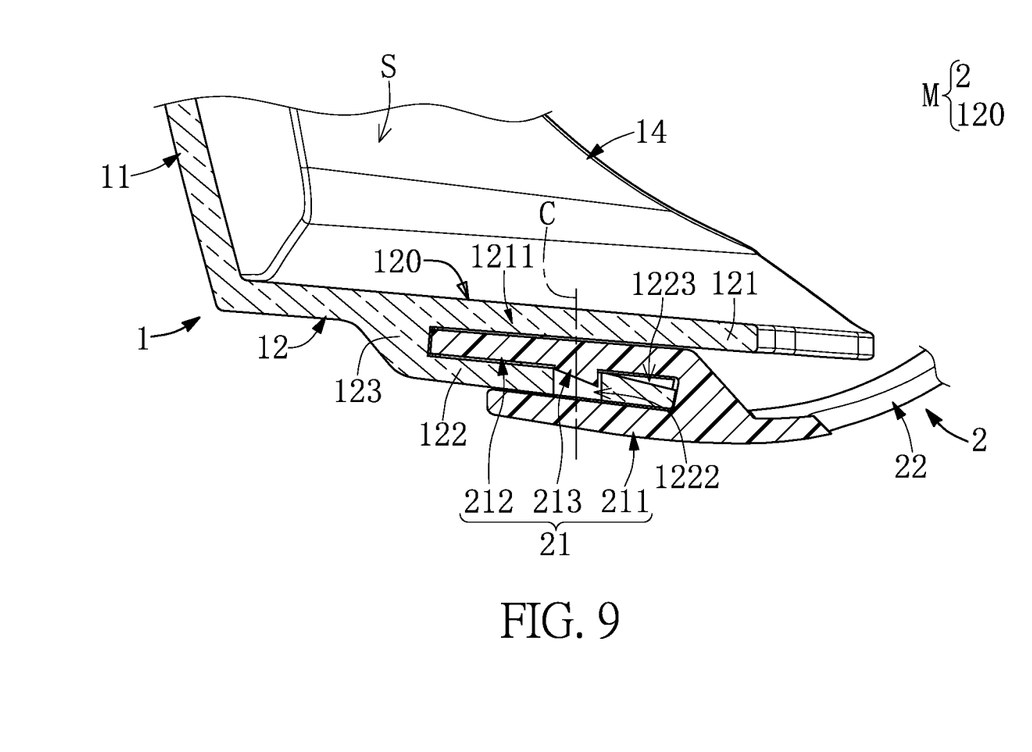
FIG. 9 is a planar cross-sectional view showing a portion of the goggle according to the first embodiment of the present disclosure.

Specifically, while the L-shaped arm 212 is inserted into the assembling slot 120, the rotation shaft 213 is moved along the guiding groove 1223 to be assembled to the shaft hole 1222, so that the assembling segment 21 can be pivotally connected to the assembling slot 120 along the axis C, but the present disclosure is not limited thereto.

Moreover, the L-shaped arm 212 of the assembling segment 21 has an engaging tooth 2121 arranged on a free end thereof, and the L-shaped arm 212 preferably has a thru-hole 2122 arranged adjacent to the engaging tooth 2121. A distance between the thru-hole 2122 and the rotation shaft 213 is at least three times of a distance between the thru-hole 2122 and the engaging tooth 2121. Accordingly, the thru-hole 2122 of the L-shaped arm 212 can provide a buffering function to the engaging tooth 2121.

Figure 10:
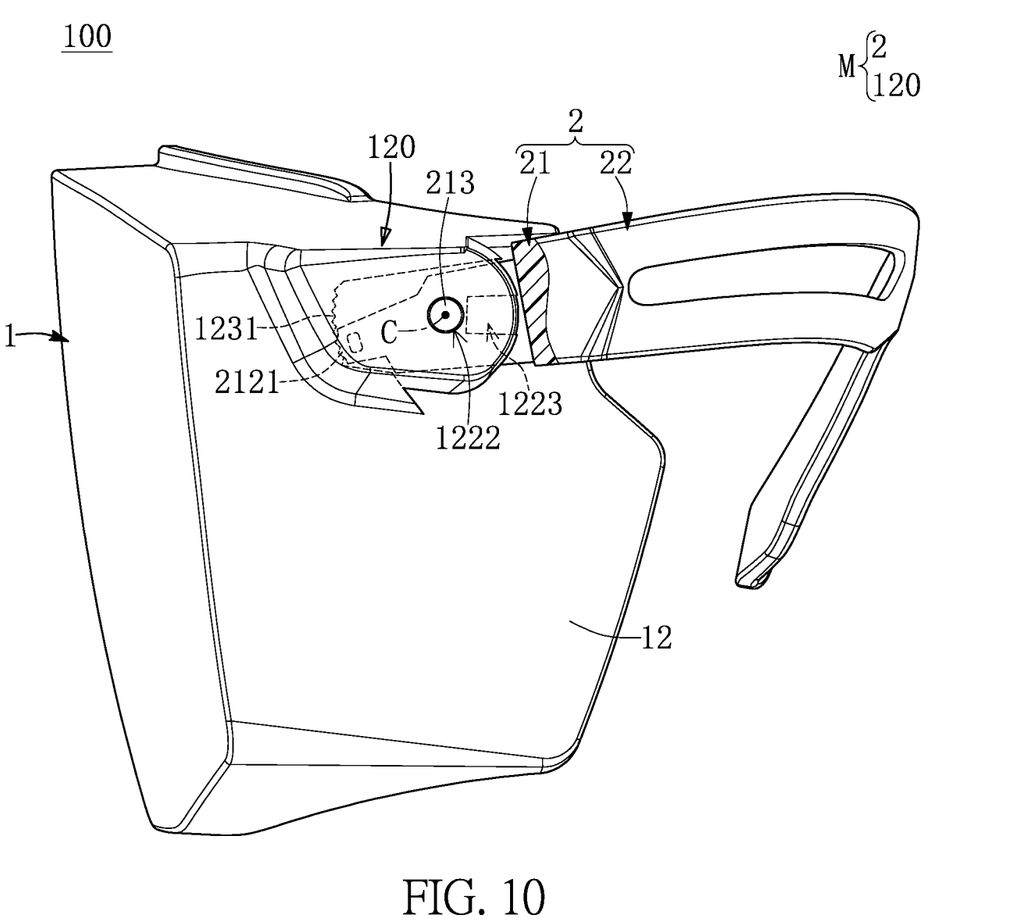
FIG. 10 is a planar view showing a bendable temple upwardly rotated relative to a lens assembly according to the first embodiment of the present disclosure.
Figure 11:
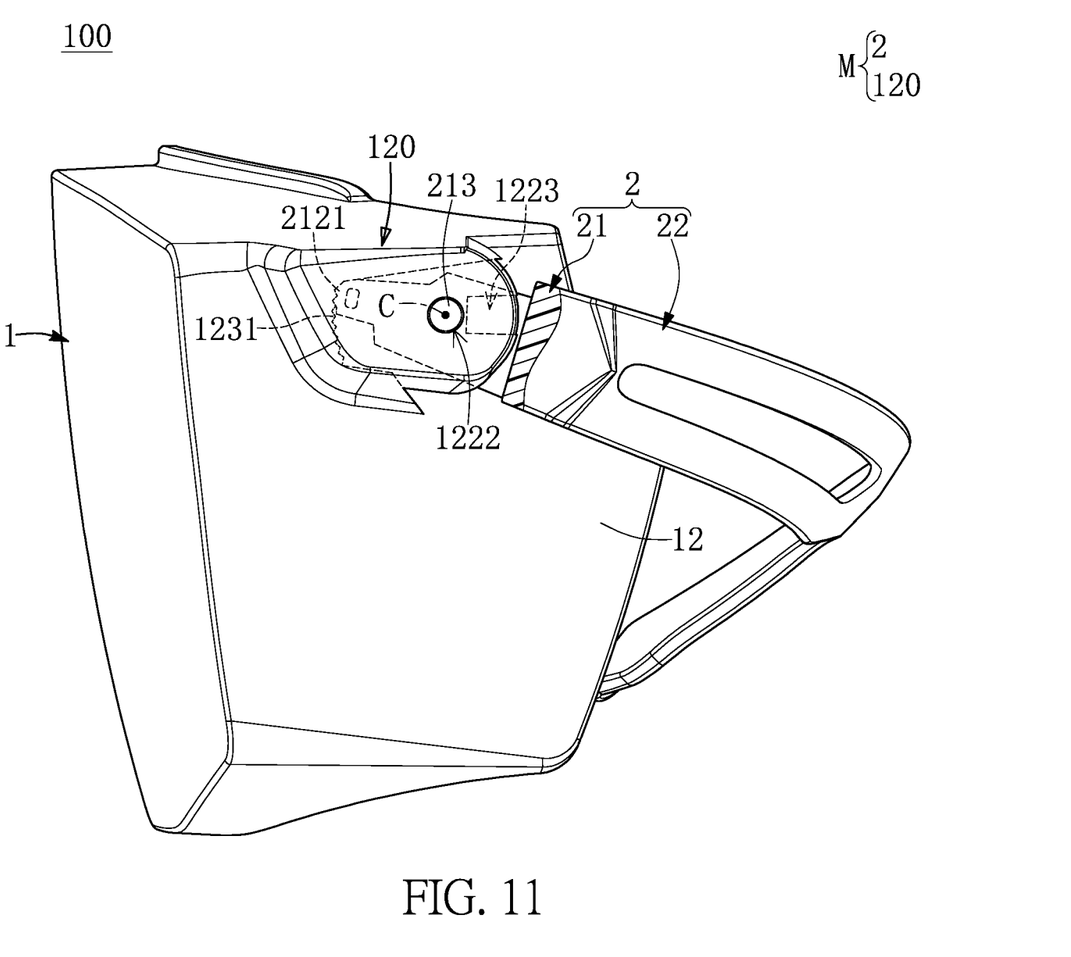
FIG. 11 is a planar view showing the bendable temple downwardly rotated relative to the lens assembly according to the first embodiment of the present disclosure.

Specifically, as shown in FIG. 10 and FIG. 11, the engaging tooth 2121 of the assembling segment 21 is inserted into the assembling slot 120 and is engaged with the retaining rack 1231, and the assembling segment 21 is rotatable relative to the assembling slot 120 in an angle range, so that the engaging tooth 2121 is engaged with and movable from one end of the retaining rack 1231 to another end of the retaining rack 1231. In the present embodiment, as shown in FIG. 5, the retaining rack 1231 has a central angle C1231 with respect to the axis C, and the central angle is substantially equal to the angle range that is within a range from 15 degrees to 30 degrees.

Accordingly, the goggle 100 of the present embodiment is provided with the angle adjustment mechanism M that is structurally simplified (e.g., the bendable temple 2 formed as a single one-piece structure is pivotally connected to the assembling slot 120 through the assembling segment 21, and the engaging tooth 2121 is movably engaged with the retaining rack 1231), thereby effectively reducing manufacturing cost thereof and probability of being damaged.

In addition, the assembling segment 21 in the present embodiment is formed as a structure shown in the drawings, but the present disclosure is not limited thereto. For example, in other embodiments of the present disclosure not shown in the drawings, a portion of the assembling segment 21 other than the engaging tooth 2121 can be omitted according to design requirements (e.g., the shielding sheet 211 or the thru-hole 2122 can be omitted); or, the rotation shaft 213 of the assembling segment 21 can be replaced by a slot or a hole, and the shaft hole 1222 of the assembling slot 120 can be replaced by a protrusion the corresponds in shape to the slot or the hole.

Second Embodiment

Figure 12:
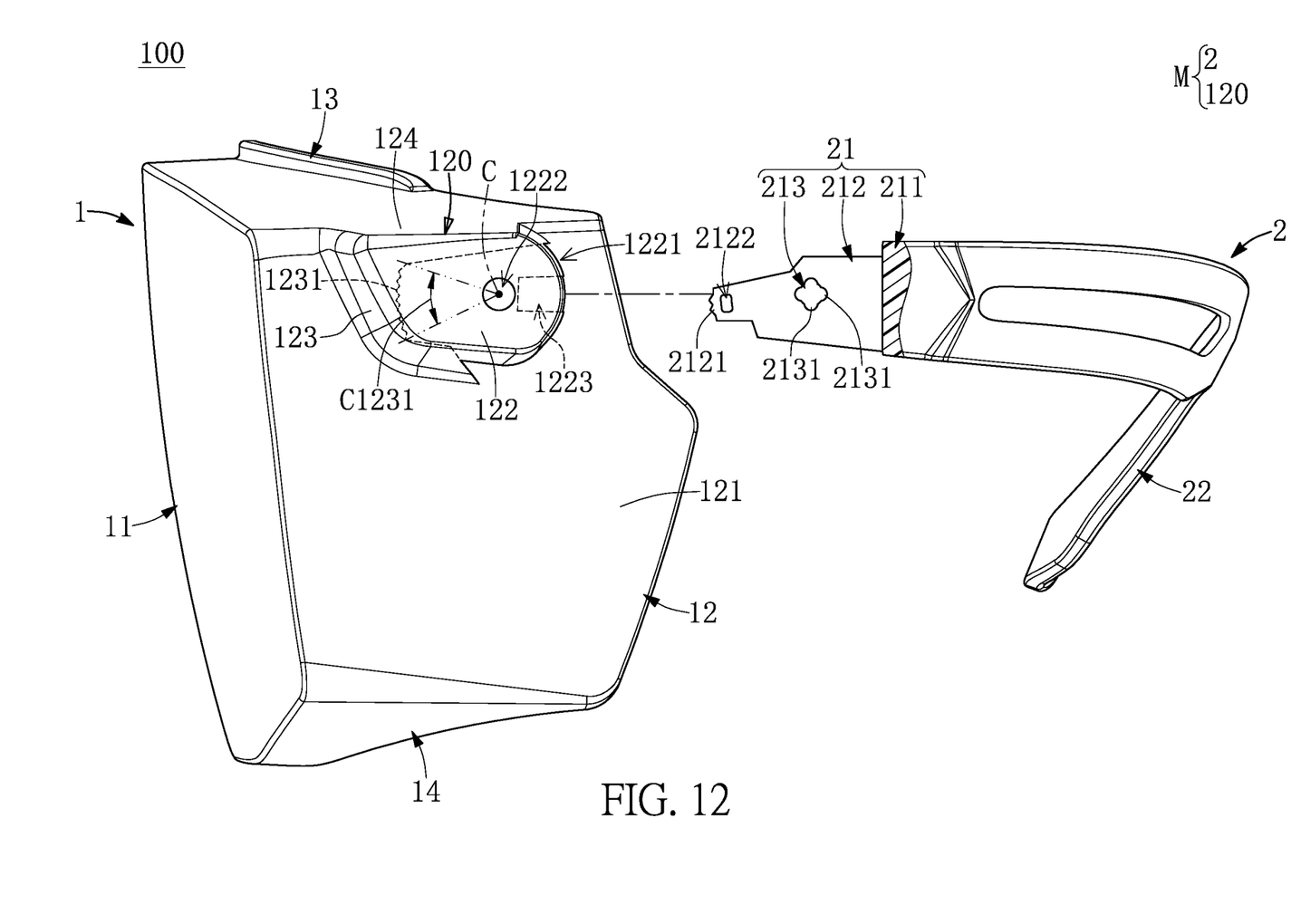
FIG. 12 is an exploded view of a goggle according to a second embodiment of the present disclosure.
Figure 13:
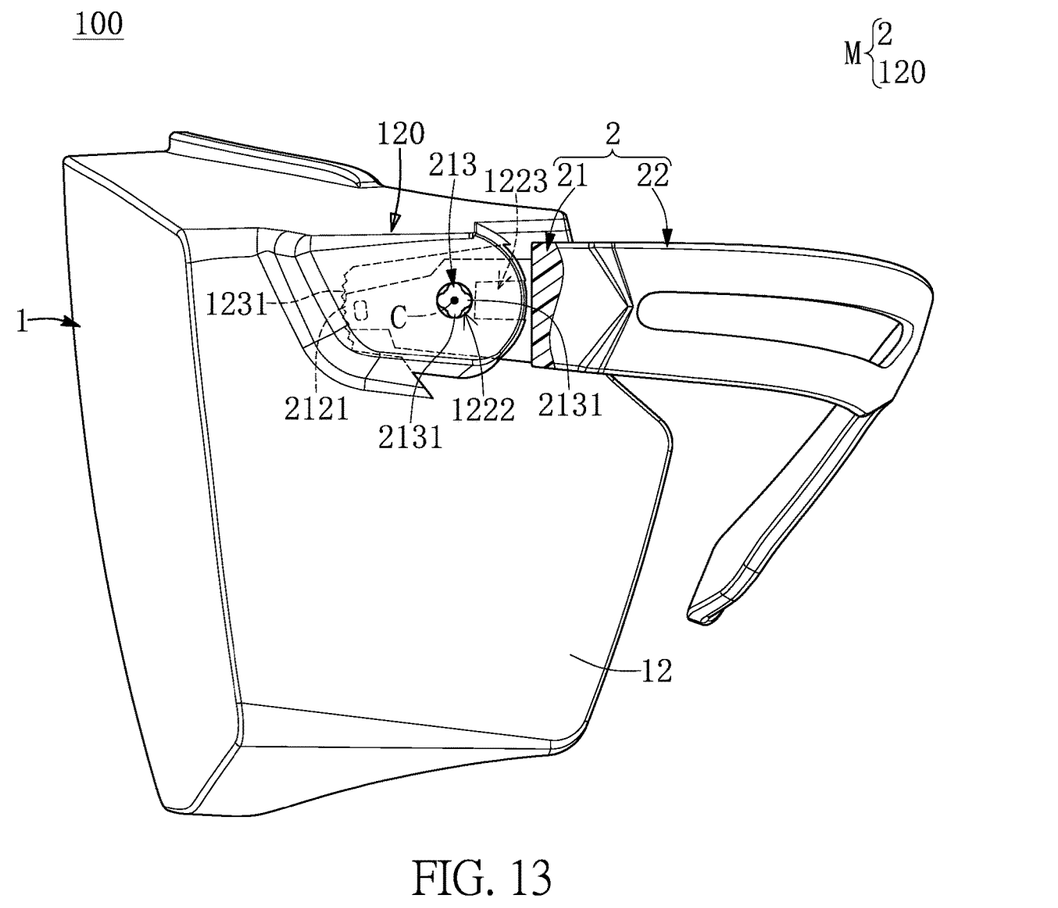
FIG. 13 is a planar view of the goggle according to the second embodiment of the present disclosure.

Referring to FIG. 12 and FIG. 13, a second embodiment of the present disclosure is similar to the first embodiment of the present disclosure. For the sake of brevity, descriptions of the same components in the first and second embodiments of the present disclosure will be omitted herein, and the following description only discloses different features between the first and second embodiments.

In the present embodiment, the rotation shaft 213 has a plurality of protrusions 2131 abutting against a wall of the shaft hole 1222. When the assembling segment 21 is rotated relative to the assembling slot 120, the protrusions 2131 are configured to scrape away any attachment (e.g., the chemical agent described in the first embodiment) on the wall of the shaft hole 1222, thereby keeping the rotation shaft 213 to smoothly rotate in the shaft hole 1222.

Beneficial Effects of the Embodiments

In conclusion, the goggle of the present disclosure is provided with the angle adjustment mechanism that is structurally simplified (e.g., the bendable temple formed as a single one-piece structure is pivotally connected to the assembling slot through the assembling segment, and the engaging tooth is movably engaged with the retaining rack), thereby effectively reducing manufacturing cost thereof and probability of being damaged.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:
1. A goggle, comprising:
a lens;
two lateral frames respectively connected to two opposite sides of the lens, wherein two sides of the two lateral frames away from each other each have a respective assembling slot, and wherein the assembling slot of each of the two lateral frames has a retaining rack arranged therein, and the retaining rack is in an arced shape and is arranged adjacent to the lens;
a top frame connected to the lens and the two lateral frames, wherein the lens, the two lateral frames, and the top frame jointly define an eye-protection space; and
two bendable temples each being integrally formed as a single one-piece structure and including an assembling segment having an engaging tooth and a flexible segment that extends from the assembling segment, wherein the assembling segments of the two bendable temples are respectively and pivotally connected to the assembling slots of the two lateral frames, and each of the two bendable temples and the corresponding assembling slot are jointly defined as an angle adjustment mechanism;
wherein in each of the two angle adjustment mechanisms, the engaging tooth of the assembling segment is inserted into the assembling slot and is engaged with the retaining rack, and the assembling segment is rotatable relative to the assembling slot in an angle range, so that the engaging tooth is engaged with and movable from one end of the retaining rack to another end of the retaining rack;

wherein each of the two lateral frames includes a main board, a limiting lateral board facing the main board, and a limiting end portion that connects the main board and the limiting lateral board, wherein in each of the two lateral frames, the assembling slot includes the limiting lateral board, the limiting end portion, and a mating portion of the main board that faces the limiting lateral board, and wherein in each of the two angle adjustment mechanisms, the retaining rack is formed on the limiting end portion, the limiting lateral board has a shaft hole, and the assembling segment has a rotation shaft assembled to the shaft hole;

wherein the assembling slot of each of the two lateral frames has a slot opening arranged on an end of the limiting lateral board away from the limiting end portion, and wherein in each of the two angle adjustment mechanisms, the limiting lateral board has a guiding groove recessed from the end thereof toward the shaft hole, the guiding groove is in spatial communication with the slot opening, and the rotation shaft is assembled into the shaft hole by being moved along the guiding groove;

wherein in each of the two lateral frames, a distance between the guiding groove and the mating portion gradually reduces in a direction from the slot opening to the shaft hole.

2. The goggle according to claim 1, wherein in each of the two angle adjustment mechanisms, the assembling segment is pivotally connected to the assembling slot along an axis, the retaining rack has a center of circle located at the axis, the retaining rack has a central angle with respect to the axis, and the central angle is substantially equal to the angle range.

3. The goggle according to claim 1, wherein in each of the two angle adjustment mechanisms, the rotation shaft has a plurality of protrusions abutting against a wall of the shaft hole, and when the assembling segment is rotated relative to the assembling slot, the protrusions are configured to scrape away any attachment on the wall of the shaft hole.

4. The goggle according to claim 1, wherein each of the two lateral frames includes a limiting top board coplanar with the top frame, and wherein in each of the two lateral frames, the limiting top board is integrally connected to the main board, the limiting end portion, and the limiting lateral board.

5. The goggle according to claim 1, wherein in each of the two angle adjustment mechanisms, the assembling segment includes an L-shaped arm inserted into the assembling slot, the engaging tooth is arranged on a free end of the L-shaped arm, and the rotation shaft is formed on an inner side of the L-shaped arm.

6. The goggle according to claim 5, wherein in each of the two angle adjustment mechanisms, the assembling segment includes a shielding sheet, the L-shaped arm is connected to the shielding sheet so as to jointly sandwich the limiting lateral board, and the shielding sheet covers the shaft hole.

7. The goggle according to claim 5, wherein in each of the two angle adjustment mechanisms, the L-shaped arm has a thru-hole arranged adjacent to the engaging tooth, and a distance between the thru-hole and the rotation shaft is at least three times of a distance between the thru-hole and the engaging tooth.

8. The goggle according to claim 1, wherein each of the two bendable temples is made of a single material, and wherein the flexible segment of each of the two bendable temples curvedly extends from the assembling segment toward the lens, so that the flexible segments of the two bendable temples contact each other.

9. The goggle according to claim 1, wherein the lens, the two lateral frames, and the top frame are light-permeable and are integrally formed as a single one-piece structure, and the angle range is within a range from 15 degrees to 30 degrees.

10. An angle adjustment mechanism of a goggle, comprising:

an assembling slot having a retaining rack arranged therein, wherein the retaining rack is in an arced shape; and a bendable temple being integrally formed as a single one-piece structure and including an assembling segment pivotally connected to the assembling slot and having an engaging tooth, and a flexible segment that extends from the assembling segment;

wherein the engaging tooth of the assembling segment is inserted into the assembling slot and is engaged with the retaining rack, and the assembling segment is rotatable relative to the assembling slot in an angle range, so that the engaging tooth is engaged with and movable from one end of the retaining rack to another end of the retaining rack;

wherein the assembling slot includes a limiting lateral board, a mating portion facing the limiting lateral board, a limiting end portion that connects the mating portion and the limiting lateral board, and wherein the retaining rack is formed on the limiting end portion, the limiting lateral board has a shaft hole, and the assembling segment has a rotation shaft assembled to the shaft hole;

wherein the assembling segment includes an L-shaped arm inserted into the assembling slot, the engaging tooth is arranged on a free end of the L-shaped arm, and the rotation shaft is formed on an inner side of the L-shaped arm.

11. The angle adjustment mechanism according to claim 10, wherein the assembling segment is pivotally connected to the assembling slot along an axis, the retaining rack has a center of circle located at the axis, the retaining rack has a central angle with respect to the axis, and the central angle is substantially equal to the angle range.

12. The angle adjustment mechanism according to claim 10, wherein the rotation shaft has a plurality of protrusions abutting against a wall of the shaft hole, and when the assembling segment is rotated relative to the assembling slot, the protrusions are configured to scrape away any attachment on the wall of the shaft hole.

13. The angle adjustment mechanism according to claim 10, wherein the assembling slot has a slot opening arranged on an end of the limiting lateral board away from the limiting end portion, wherein the limiting lateral board has a guiding groove recessed from the end thereof toward the shaft hole, the guiding groove is in spatial communication with the slot opening, and the rotation shaft is assembled into the shaft hole by being moved along the guiding groove, and wherein a distance between the guiding groove and the mating portion gradually reduces in a direction from the slot opening to the shaft hole.

14. The angle adjustment mechanism according to claim 10, wherein the assembling segment includes a shielding sheet, the L-shaped arm is connected to the shielding sheet so as to jointly sandwich the limiting lateral board, and the shielding sheet covers the shaft hole, and wherein the L-shaped arm has a thru-hole arranged adjacent to the engaging tooth, and a distance between the thru-hole and the rotation shaft is at least three times of a distance between the thru-hole and the engaging tooth.

15. The angle adjustment mechanism according to claim 10, wherein the bendable temple is made of a single material, and the angle range is within a range from 15 degrees to 30 degrees.

16. An angle adjustment mechanism of a goggle, comprising:
- an assembling slot having a retaining rack arranged therein, wherein the retaining rack is in an arced shape; and
- a bendable temple being integrally formed as a single one-piece structure and including an assembling segment pivotally connected to the assembling slot and having an engaging tooth, and a flexible segment that extends from the assembling segment;
- wherein the engaging tooth of the assembling segment is inserted into the assembling slot and is engaged with the retaining rack, and the assembling segment is rotatable relative to the assembling slot in an angle range, so that the engaging tooth is engaged with and movable from one end of the retaining rack to another end of the retaining rack;
- wherein the assembling slot includes a limiting lateral board, a mating portion facing the limiting lateral board, a limiting end portion that connects the mating portion and the limiting lateral board, and wherein the retaining rack is formed on the limiting end portion, the limiting lateral board has a shaft hole, and the assembling segment has a rotation shaft assembled to the shaft hole;
- wherein the rotation shaft has a plurality of protrusions abutting against a wall of the shaft hole, and when the assembling segment is rotated relative to the assembling slot, the protrusions are configured to scrape away any attachment on the wall of the shaft hole.

\* \* \* \* \*